United States Patent [19]

Labrie

[11] Patent Number: 4,760,053

[45] Date of Patent: Jul. 26, 1988

[54] COMBINATION THERAPY FOR SELECTED SEX STEROID DEPENDENT CANCERS

[76] Inventor: Fernand Labrie, 2735 boul. Liègeois, Ste-Foy, Quebec, Canada, G1W 1Z9

[21] Appl. No.: 892,214

[22] Filed: Jul. 31, 1986

[30] Foreign Application Priority Data

Aug. 2, 1985 [WO] PCT Int'l Appl. .................. PCT/US85/01454

[51] Int. Cl.$^4$ ............................................. A61K 37/43
[52] U.S. Cl. ...................... 514/15; 514/177; 514/178; 514/800; 514/358
[58] Field of Search ................ 530/328, 313; 514/178, 514/800, 177, 358, 15

[56] References Cited

U.S. PATENT DOCUMENTS

| | | | |
|---|---|---|---|
| 4,024,248 | 5/1977 | König et al. | 424/177 |
| 4,071,622 | 1/1978 | Johnson et al. | 424/177 |
| 4,094,994 | 6/1978 | Schönenberger et al. | 424/177 |
| 4,097,578 | 6/1978 | Perronnet et al. | 424/273.2 |
| 4,100,274 | 7/1978 | Du Ha et al. | 424/177 |
| 4,118,483 | 10/1978 | König et al. | 4214/177 |
| 4,234,571 | 11/1980 | Nestor et al. | 514/15 |
| 4,239,776 | 12/1980 | Glen et al. | 424/304 |
| 4,291,028 | 9/1981 | Vorys | 514/177 |
| 4,292,315 | 9/1981 | Vorys | 514/178 |
| 4,329,364 | 5/1982 | Neri et al. | 424/324 |
| 4,386,080 | 5/1983 | Crowley et al. | 424/209 |
| 4,415,553 | 11/1983 | Zhabilov et al. | 530/358 |
| 4,472,382 | 9/1984 | Labrie et al. | 424/177 |
| 4,481,190 | 11/1984 | Nestor et al. | 530/313 |
| 4,530,920 | 7/1985 | Nestor et al. | 530/328 |
| 4,632,979 | 12/1986 | Coy et al. | 530/313 |
| 4,650,787 | 3/1987 | Schally et al. | 530/311 |
| 4,667,014 | 5/1987 | Nestor, Jr. et al. | 514/800 |

FOREIGN PATENT DOCUMENTS

| | | |
|---|---|---|
| 637389 | 3/1964 | Belgium . |
| 58481 | 8/1982 | European Pat. Off. . |
| 78158 | 5/1983 | European Pat. Off. . |

OTHER PUBLICATIONS

Cancer Treatment Reports, vol. 68 (No. 1) pp. 281–289 (1984), A. V. Schally et al.
Proc. Natl. Acad. Sci. U.S.A., vol. 80, pp. 1459–1462 (1983), T. W. Redding and A. V. Schally.
"LH–RH Analogs in the Treatment of Human Breast Cancer", H. A. Harvey et al. in *LHRH and Its Analogs*-A New Class of Contraceptive and Therapeutic Agents, pp. 329–335 (B. H. Vickery et al. etc.) MTP Press Lancaster URI.
Lancet, 1, 1213–1216 (1982), J. G. M. Klijn et al. (The Lancet, May 29, 1982).
Cancer, vol. 50, 1708–1712 (1982), A. V. Buzdar et al.
Lancet, 1204–1207 (1973), H. Flax et al. (The Lancet; Jun. 2, 1973).
The Prostate, vol. 4, 579–594 (1983), F. Labrie et al.
J. Steroid Biochem., vol. 19, 99–1007 (1983), F. Labrie et al.
Cancer Treatment Review, vol. 5, 131–141 (1978), H. Movridsen et al.
J. Steroid Biochem. vol. 20 (No. 6B) 1381 (1984), J. G. M. Klijn et al.
J. Med. Chem., vol. 21, 1018–10214 (1978), A. S. Dutta et al.
Biochem. Biophy. Res. Commun., vol. 100, pp. 915–920 (1981), J. Erchegg et al.

List continued on next page.

*Primary Examiner*—Delbert R. Phillips
*Attorney, Agent, or Firm*—Ostrolenk, Faber, Gerg & Soffen

[57] ABSTRACT

A combination therapy for treatment of selected sex steroid dependent cancers in susceptible warm-blooded animals comprising administering to such animals whose hormone output of their testes or ovaries, respectively, is blocked a therapeutically effective amount of an antiandrogen and/or an antiestrogen and/or at least one inhibitor of sex steroid biosynthesis or pharmaceutical compositions thereof wherein the selected sex steroid dependent cancer are, for example, testicular cancer, ovarian cancer, renal cancer or uterine cancer is disclosed.

13 Claims, 3 Drawing Sheets

OTHER PUBLICATIONS

Endrocrinology, vol. 110, pp. 1445-1447 (1982); D. H. Coy et al.

J. Steroid Biochem., vol. 20 (No. 6B), 1366 (1984); J. I. Nestor et al.

J. Steroid Biochem. vol. 20, (No. 6B) 1365 (1984); J. Rivier et al.

J. Steroid Biochem., vol. 20 (No. 6B) p. 1369 (1984); A. Corbin et al.

LH-RH and Its Analogs (B. H. Vickery et al. Editors), pp. 3-10, J. J. Nestor.

LH-RH and Its Analogs (B. H. Vickery et al. Editors), pp. 11-22, J. Rivier et al.

LH-RH and Its Analogs (B. H. Vickery et al. Editors) pp. 23-33, J. J. Nestor et al.

"Solid Phase Peptide Synthesis" Stewart et al. Freman and Co., San Francisco, Calif. (1969). pp. 1-26.

J. Med. Chem. vol. 19, pp. 423-425 (1976) D. H. Coy et al.

LHRH and Its Analogs (B. H. Vickery et al, eds.) pp. 337-350, N. Faure et al.

LH-RH and Its Analogs (B. H. Vickery et al, eds.), pp. 351-364, R. J. Santen et al.

J. Steroid Biochem., vol. 20 (No. 6B) p. 1375 (1984); R. Santen et al.

J. Steroid Biochem, vol. 20 (No. 6B) p. 1395 (1984); D. Kerle et al.

Abstr. 7th Internat'l Cong. Endocrin., Excerpta Medica (1984) p. 98; F. Labrie et al.

J. Androl., vol. 1, pp. 209-228 (1984); F. Labrie et al.

Lancet, I, pp. 971-972 (1984); Kahan et al.

COMBINATION THERAPY FOR SELECTED SEX STEROID DEPENDENT CANCERS

CROSS-REFERENCE TO RELATED APPLICATIONS

This Application is related to the following copending U.S. patent applications: Ser. Nos. 636,883, filed Aug. 2, 1984; 699,702, filed Feb. 8, 1985, now U.S. Pat. No. 4,666,885; 699,710, filed Feb. 8, 1985; and 699,711, filed Feb. 8, 1985, now U.S. Pat. No. 4,659,695.

BACKGROUND OF THE INVENTION

This invention relates to a combination therapy for selected sex steroid dependent cancers in susceptible warm-blooded animals including humans comprising administering to such animals whose hormone output of their testes or ovaries, respectively, is blocked a therapeutically effective amount of an antiandrogen and/or an antiestrogen and/or at least one inhibitor of sex steroid biosynthesis, or pharmaceutical compositions thereof, wherein the selected sex steroid dependent cancers are testicular cancer, ovarian cancer, colon-rectal cancer, renal cancer, pancreatic cancer, liver cancer, stomach cancer, skin cancer, uterine cancer, brain cancer or larynx cancer. The hormone output of the animal's testes or ovaries, respectively, can be blocked by surgical or chemical means. (In post-menopausal women the attending clinician may decide that the hormone output of the ovaries need not be blocked.)

U.S. patent application Ser. No. 638,883 relates to the treatment of female breast cancer by use of a combination therapy comprising administering an antiandrogen and an antiestrogen to female after the hormone output of her ovaries has blocked by chemical or surgical means.

U.S. patent application Ser. No. 699,702 relates to the treatment of female breast cancer by use of a therapy comprising administering to a female after the hormone output of her ovaries has been blocked by chemical or surgical means an antiandrogen and optionally an inhibitor of sex steroid biosynthesis.

U.S. patent application Ser. No. 699,710 relates to a treatment of male breast cancer by using a therapy comprising administering to a male after the hormone output of his testes has been blocked by chemical or surgical means an antiandrogen and optionally at least one inhibitor of sex steroid biosynthesis.

U.S. patent application Ser. No. 699,711 relates to a treatment of prostate cancer by use of a combination therapy comprising administering an antiandrogen and at least one inhibitor of sex steroid biosynthesis to a male after the hormone output of his testes has been blocked by chemical or surcical means.

While various investigators have been studying hormone-dependent breast and prostate cancer, none have proposed the combination therapy of this invention.

A. V. Schally et al., Cancer Treatment Reports, 68, (No. 1) 281-289 (1984), summarize the results of animal and clinical studies on growth inhibition of hormone-dependent mammary and prostate tumors by use of analogues of luteinizing hormone-releasing hormones, the so-called LH-RH agonists and suggest that LH-RH analogs and/or antagonists may have potential for treating breast cancer.

T. W. Redding and A. V. Schally, Pro. Natl. Acad. Sci. USA, 80, 1459-1462 (1983), disclose reduction of estrogen-dependent mammary tumors in rats and mice by use of an LH-RH agonist, [D-Trp[6]]LH-RH or of two specific antagonists and inhibition of prostate tumor growth in rats of chronic use of an LH-RH agonist, [D-Trp[6]]LH-RH.

In U.S. Pat. No. 4,071,622, it is disclosed that use of certain LH-RH agonists causes regression of DMBA-induced mammary carcinoma in rats.

In U.S. Pat. No. 4,472,382, it is disclosed that prostate adenocarcinoma, benign prostate hypertrophy and hormone-dependent mammary tumors may be treated with various LH-RH agonists and that prostate adenocarcinoma and benign hypertrophy may be treated by use of various LH-RH agonists and an antiandrogen. However, there is no suggestion or disclosure of the present invention.

Some clinical improvement in premenopausal women with breast cancer by use of the two LH-RH agonists, Buserelin and Leuprolide, is also reported by H. A. Harvey et al. "LH-RH analogs in the treatment of human breast cancer", *LH-RH and its Analogs—A New Class of Contraceptive and Therapeutic Agents* (B. H. Vickery and J. J. Nestor, Jr., and E. S. E. Hafez, eds) Lancester, MTP Press, (1984) and by J. G. M. Klijn et al. "Treatment with luteinizing hormone releasing hormone analogue (Buserelin) in premenopausal patients with metastatic breast cancer", Lancet, 1, 1213-1216 (1982).

Treatment of advanced breast cancer with aminoglutethimide after therapy with the antiestrogen, Tamoxifen is disclosed by A. V. Buzdar et al., Cancer, 50, 1708-1712 (1982).

H. Flax et al., Lancet, 1204-1207, (1973), suggest some women's breast cancers are androgen-dependent.

In U.S. Pat. No. 4,329,364, it is disclosed that the antiandrogen, 4'-nitro-3'-trifourormethyl isobutyranilide may be used for treatment of prostatic cancer.

Some clinical improvement in men with prostate cancer by use of the two LH-RH agonists, Buserelin and Leuprolide, is also reported by N. Faure et al. at pages 337-350 and by R. J. Santen et al. at pages 351-364, respectively, *LH-RH and its Analogs—A New Class of Contraceptive and Therapeutic Acents* (B. H. Vickery and J. J. Nestor, Jr., and E. S. E. Hafez, eds) Lancester, MTP Press, (1984).

R. Santen et al., The Journal of Steroid Biochemistry, Volume 20, No 6B, at page 1375 (1984), disclose that use of ketoconazole in combination with chronic administration of Leuprolide in rodents decreased basal and Leuprolide stimulated testosterone levels.

D. Kerle et al., The Journal of Steroid Biochemistry, Volume 20, No 6B, at page 1395 (1984) disclose that the combined use of a LH-RH analogue and ketoconazole produced objective responses in some prostate cancer patients who have relapsed or failed to respond to treatment with a LH-RH analogue alone.

F. Labrie et al., Abstracts of 7th International Congress of Endrocrinology, Excerpta Medica (1984) at page 98 discloses that treatment of prostate cancer patients with LH-RH agonists alone causes a transient increase in serum androgen levels lasting for 5 to 15 days before castration levels are reached.

F. Labrie et al., The Prostate, 4, 579-594 (1983), disclose that use of a combination therapy of an LH-RH agonist (Buserelin) and an antiandrogen (Anandron) to treat advanced prostate cancer in previously untreated patients effects simultaneous inhibition of androgens of both testicular and adrenal origin.

F. Labrie et al., J. Steroid Biochem., 19, 99–1007 (1983), disclose the treatment of prostate cancer by the combined administration of an LH-RH agonist and an antiandrogen. Labrie et al. disclose animal and clinical data in support of the proposition that the combined LH-RH/antiandrogen treatment neutralizes the stimulatory influence of all androgens on the development and growth of androgen-dependent prostatic cancer.

In U.S. Pat. No. 4,094,994, it is disclosed that the use of antiestrogens such as meso-3,4-bis(3'-hydroxyphenyl)hexane inhibits MCF7 human breast tumor cells. In fact, the inhibitory activity of the antiestrogen was antagonized by estradiol.

H. Mouridsen et al., Cancer Treatment Review 5, 131–141, (1978), disclose that Tamoxifen, an antiestrogen is effective in remission of advanced breast cancer in about 30% of the patients treated.

J. G. M. Klijn et al., (J. Steroid Biochem, Vol. 20 (No. 6B), 1381 (1984), disclosed the combined use of the antiestrogen, Tamoxifen, and the LH-RH agonist, Buserelin, for treatment of breast cancer is known, but objective remission of such cancers remains low (35%).

SUMMARY OF THE INVENTION

The invention provides a method of treating selected sex steroid dependent cancers in a warm-blooded animal which comprises administering a therapeutically effective amount of an antiandrogen and/or an antiestrogen and/or at least one inhibitor of sex steroid biosynthesis or pharmaceutical compositions thereof to the animal whose hormone output of the testes or ovaries, is blocked. The invention also provides a method of treating selected sex steroid dependent cancers which comprises administering a therapeutically effective amount (1) of an antiandrogen or (2) of at least one inhibitor of sex steroid biosynthesis or (3) of an antiandrogen and an antiestrogen or (4) of an antiandrogen and at least one inhibitor of sex steroid biosynthesis or (5) of an antiestrogen and at least one inhibitor of sex steroid biosynthesis or (6) of an antiandrogen and an antiestrogen and at least one inhibitor of sex steroid biosynthesis or pharmaceutical composition thereof, wherein the sex steroid dependent cancers are testicular cancer, ovarian cancer, colon-rectal cancer, renal cancer, pancreatic cancer, liver cancer, stomach cancer, skin cancer, uterine cancer, brain cancer or larynx cancer.

The present invention provides a new combination therapy of selected sex steroid dependent cancers which inhibits tumor growth and metastases and causes in some instances complete remission. The invention is exemplified by detailed discussion of the therapy of uterine cancer and renal cancer. The therapy of other selected sex steroid dependent cancers (listed above) is carried out analogously.

In one aspect, the invention provides a method of treating selected sex steroid dependent cancers such as, for example, uterine cancer in a warm-blooded female animal in need of such treatment which comprises administering to said animal whose hormone output of the ovaries is blocked, a therapeutically effective amount of an antiandrogen or a pharmaceutical composition thereof. The ovarian hormonal secretions of said animal can be blocked by surgical or chemical means. In one aspect, the invention provides a method of treating selected sex steroid dependent cancers such as, for example, uterine cancer in a castrated warm-blooded female animal, i.e., such a female animal whose ovaries are blocked by surgical or chemical means from secreting estrogen, which comprises administering to such a female in need of such treatment an antiandrogen in association with at least one inhibitor of sex steroid biosynthesis and, optionally, an antiestrogen, or pharmaceutical compositions thereof, in amounts sufficient to treat such cancers, e.g., uterine cancer. In another aspect, the invention provides a method of treating selected sex steroid dependent cancers such as, for example, uterine cancer in a warm-blooded female animal in need of such treatment which comprises blocking the ovarian hormonal secretions of said animal by surgical or chemical means and administering to said animal therapeutically effective amounts of an antiestrogen in association with at least one inhibitor of sex steroid biosynthesis, or pharmaceutical compositions thereof. In one aspect, the invention provides a method of treating selected sex steroid dependent cancers such as, for example, uterine cancer in a warm-blooded female animal whose ovaries are blocked by surgical or chemical means from secreting estrogen, which comprises administering to an animal in need of such treatment an antiandrogen and an antiestrogen, or pharmaceutical compositions thereof, in amounts sufficient to treat such cancers, e.g., uterine cancer. In another aspect of the present invention, there is provided a a combination of pharmaceutical compositions for combination therapy of selected sex steroid dependent cancers in a warm-blooded animal whose hormone output of the testes or ovaries is blocked, the combination consisting of pharmaceutical compositions comprising an antiestrogen and at least one inhibitor of sex steroid biosynthesis or an antiandrogen and antiestrogen or an antiandrogen and at least one inhibitor of sex steroid biosynthesis or an antiandrogen and an antiestrogen and at least one inhibitor of sex steroid biosynthesis wherein the selected sex steroid dependent cancers are testicular cancer, ovarian cancer, colon-rectal cancer, renal cancer, pancreatic cancer, liver cancer, stomach cancer, skin cancer, uterine cancer, brain cancer or larynx cancer.

DETAILED DESCRIPTION OF THE INVENTION

By completely blocking sex steroids (androgens and estrogens) production and/or action, the present invention provides a method of inhibiting the growth of sex steroid-sensitive tumors, e.g., uterine tumors in warm-blooded animals having such tumors.

In female mammals, the ovaries may be surgically removed (oophorectomy) but preferably the secretion of estrogens from the ovaries is blocked by chemical castration by administering an effective amount of an LH-RH agonist or antagonist. Thus, in a preferred aspect, the present invention provides a method of treating selected sex steroid dependent cancers such as, for example, uterine cancer in a warm-blooded female animal, which comprises administering to such a female in need of such treatment an LH-RH agonist or antagonist, in association with an antiandrogen and/or an antiestrogen and/or at least one inhibitor of sex steroid biosynthesis according to the invention, preferably an antiandrogen. Preferably in this treatment at least one inhibitor of sex steroid biosynthesis, or pharmaceutical compositions thereof, and/or antiestrogen is administered.

In its preferred aspect, the LH-RH agonist is administered parenterally (subcutaneously or intramuscularly or intranasally) and, in association therewith, the antiandrogen and the inhibitor of sex steroid biosynthesis and/or antiestrogen are each administered orally.

Thus, this invention provides a novel method for effective treatment of selected sex steroid dependent cancers such as, for example, uterine cancer, in the absence of antiestrogen. In addition, the amounts of antiestrogen required when administered in association with this combined therapy are lower than normally used in prior art methods, e.g., J. G. M. Klijn et al., J. Steroid Biochem. 20 (No. 6B) 1381 (1984), to treat breast cancer, and thus, the harmful effects of relatively large doses of antiestrogen are minimized.

In one preferred aspect, the present invention provides an effective method of treating selected sex steroid dependent cancers such as, for example, uterine cancer in warm-blooded female animals in need of such treatment by administering an LH-RH agonist or antagonist, in association with an antiandrogen and an inhibitor of sex steroid biosynthesis or pharmaceutical compositions thereof in amounts sufficient to inhibit tumor growth. These active compounds can be administered together or in any order as discussed hereinafter.

To assist in determining the effect of the treatment, blood plasma concentrations of the sex steroids of adrenal and ovarian origin, i.e., precursor steroids, androgens and estrogens, and tumor size are measured. Lowered concentrations of sex steroids and reduction in tumor size are indicative of successful treatment, e.g. inhibition of tumor growth using active compounds described herein in accordance with the present invention. The concentrations of adrenal androgens and estrogens such as dehydroepiandrosterone (DHEA), DHEADsulfate (DHEAS), androst-5-ene-$3\beta$, $17\beta$-diol ($\Delta^5$-diol) and, the ovarian estrogen, $17\beta$-estradiol ($E_2$) are measured by standard methods well known to those skilled in the art, see for example F. Labrie et al., The Prostate, 4, 579–594 (1983).

The change in tumor size is measured by standard physical methods well known to those skilled in the art, e.g., bone scan, chest X-ray, skeletal survey, ultrasonography of the liver and liver scan (if needed), CAT-scan and physical examination.

While a LH-RH agonist or a LH-RH antagonist may be used in one preferred aspect of the present invention, the use of a LH-RH agonist is more preferred.

In another aspect, the invention provides a method of treating selected sex steroid dependent cancers such as, for example, renal cancer in a warm-blooded male animal in need of such treatment which comprises blocking the testicular hormonal secretions of said animal by surgical or chemical means and administering to said animal a therapeutically effective amount of an antiandrogen, or a pharmaceutical composition thereof. In another aspect, the invention provides a method of treating selected sex steroid dependent cancers such as, for example, renal cancer in a castrated warm-blooded male animal, i.e., such a male animal whose testes are blocked by surgical or chemical means from secreting androgen, which comprises administering to an animal in need of such treatment therapeutically effective amounts of an antiandrogen in association with at least one inhibitor of sex steroid biosynthesis, or a pharmaceutical composition thereof, in an amount sufficient to treat the cancer. In another aspect, the invention provides a method of treating selected sex steroid dependent cancers such as, for example, renal cancer in a castrated warm-blooded male animal, which comprises administering to an animal in need of such treatment therapeutically effective amounts of an antiandrogen and an antiestrogen, optionally in association with at least one inhibitor of sex steroid biosynthesis. By simultaneously blocking sex-steroids (androgens and estrogens of testicular and adrenal origin) production and/or action, the present invention provides a method of inhibiting the growth of sex steroid-sensitive tumors in warm-blooded male animals having such tumors.

In male mammals, the removal of testicular androgens may be achieved by surgical castration (orchiectomy) but preferably the secretion of androgens from the testes is blocked by chemical castration by administering to the warm-blooded male animal, an effective amount of an LH-RH agonist or antagonist. Thus, in a preferred aspect, the present invention provides a method of treating selected sex steroid dependent cancers such as, for example, renal cancer in a warm-blooded male animal, which comprises administering to an animal in need of such treatment an LH-RH agonist or antagonist in association with an antiandrogen and/or an antiestrogen and/or at least one inhibitor of sex steroid biosynthesis as discussed in the preceding paragraph, preferably in association with an antiandrogen, or a pharmaceutical composition thereof, in amounts sufficient to treat the cancer.

In its preferred aspect, the LH-RH agonist or antagonist is administered parenterally (sub-cutaneously or intramuscularly) and the antiandrogen, the antiestrogen and the inhibitor(s) of sex steroid biosyntesis (if used) are administered orally.

In one preferred aspect, the present invention provides an effective method of treating selected sex steroid dependent cancers such as, for example, renal cancer in warm-blooded male animals in need of such treatment by administering a LH-RH agonist or antagonist in association with an antiandrogen or pharmaceutical compositions thereof in amounts sufficient to inhibit tumor growth. The use of an LH-RH agonist in association with an antiandrogen produced almost complete blockage of testicular steroid secretion while simultaneously blocking about 25 to 60% of the precursor sex steroids (androgens and estrogens) of adrenal origin. In still another preferred aspect, at least one inhibitor of sex steroid biosynthesis is administered to warm-blooded male animals having selected sex steroid dependent cancers such as, for example, renal cancer in association with surgical castration or chemical castration (by use of an LH-RH agonist or antagonist) and the antiandrogen. These active compounds can be administered together or in any order as discussed hereinafter.

To assist in determining the effect of the treatment, blood plasma concentrations of the testical and adrenal androgens and estrogens and tumor size are measured. Lowered concentrations of sex steroids and precursors and reduction in tumor size are indicative of successful treatment, e.g. inhibition of tumor growth. The concentrations of adrenal androgens and estrogens such as dehydroepiandrosterone (DHEA), DHEA-sulfate (DHEAS), androst-5-ene-3β, 17β-diol (Δ$^5$-diol) and, the estrogen, 17β-estradiol (E$_2$) are measured by standard methods well known to those skilled in the art, see for example F. Labrie et al., The Prostate, 4, 579–594 (1983).

The active compounds described herein and used in accordance with the present invention exhibited tumor growth inhibition and lowered concentrations of selected sex steroids when tested in warm-blooded male animals including man.

The change in tumor size is measured by standard physical methods well known to those skilled in the art, e.g., bone scan, chest X-ray, skeletal survey, ultrasonography of the liver and liver scan (if needed), CAT-scan and physical examination.

While a LH-RH agonist or a LH-RH antagonist may be used in one preferred aspect of the present invention, the use of a LH-RH agonist is more preferred.

In another aspect, the invention provides a method of treating selected sex steroid dependent cancers such as, for example, renal cancer in a warm-blooded male animal including humans in need of such treatment which comprises blocking the testicular hormonal secretions of said animal by surgical or chemical means and administering to said animal a therapeutically effective amount of an antiandrogen in assoication with at least one inhibitor of sex steroid biosynthesis, or pharmaceutical compositions thereof. By simultaneously blocking androgens of testicular and adrenal origin production and/or action, the present invention provides a method of inhibiting the growth of selected sex steroid-sensitive carcinomas in warm-blooded male animals having such carcinomas.

In a preferred aspect, the present invention provides a method of treating selected sex steroid dependent cancers such as, for example, renal cancer in a warm-blooded male animal having such cancer, which comprises administering to said animal therapeutically effective amounts of an LH-RH agonist or antagonist in association with an antiandrogen and at least one inhibitor of sex steroid biosynthesis, or pharmaceutical compositions thereof.

In its preferred aspect, the LH-RH agonist is administered parenterally (subcutaneously or intramuscularly) and the antiandrogen and the inhibitor(s) or inhibitors of sex steroid biosynthesis are each administered orally.

In one preferred aspect, the present invention provides an effective method of treating selected sex steroid dependent cancers such as, for example, renal cancer in warm-blooded male animals in need of such treatment by administering a LH-RH agonist or antagonist in association with an antiandrogen and an inhibitor of sex steroid biosynthesis of testicular origin or pharmaceutical compositions thereof in amounts sufficient to inhibit such cancer. By use of an inhibitor of testicular sex steroid biosynthesis in association with an antiandrogen and a LH-RH agonist or antagonist more complete androgen blockage is effected at an early stage in the treatment of such cancer than achieved by prior art methods. If an inhibitor of sex steroid biosynthesis of both testicular and adrenal origin (such as, for example, aminoglutethimide) is used, the administration of the inhibitor is started on the first day of treatment and continued thereafter to block adrenal steroid synthesis.

In another preferred aspect, the use of an LH-RH agonist or antagonist in association with an antiandrogen and two inhibitors of sex steroid biosynthesis, e.g. an inhibitor of adrenal sex steroid biosynthesis such as aminoglutethimide and an inhibitor of testicular sex steroid biosynthesis such as ketoconazole, produced almost complete blockage of testicular steroid secretion while simultaneously blocking the precursor sex steroids (androgens and estrogens) of adrenal origin at an early stage of the treatment. While such complete blockage of androgen secretion and/or action has not been achieved by prior art methods, such complete blockage can be achieved and maintained throughout the period of treatment in accordance with the present invention. These active compounds can be administered together or in any order as discussed hereinafter.

To assist in determining the effect of the treatment, blood plasma concentrations of the adrenal and testical androgens and estrogens and parameters of cancer evolution are measured according to known methods. Lowered concentrations of sex steroids and reduction in tumor size are indicative of successful treatment, e.g. inhibition of renal cancer cell growth. The concentrations of adrenal steroids such as dehydroepiandrosterone (DHEA), DHEA-sulfate (DHEAS), androst-5-ene-3β, 17β-diol (Δ$^5$-diol) and, the estrogen, 17β-estradiol (E$_2$) are measured by standard methods well known to those skilled in the art, see for example F. Labrie et al., The Prostate, 4, 579–594 (1983).

Objective assessment of the effect of the treatment is measured by standard physical methods well known to those skilled in the art, e.g., bone scanning, X-ray, skeletal survey, intravenous pyelography, CAT-scan and physical examination.

The use of therapeutically effective amounts of the inhibitor of testicular sex steroid biosynthesis such as ketoconazole or aminoglutethimide in association with the antiandrogen and the LH-RH agonist or LH-RH antagonist in accordance with the present invention effectively surpresses the serum sex steroid levels, especially serum testosterone and dihydrotestosterone concentrations stimulated by treatment with LH-RH agonist at the start of the treatment even in the presence of an antiandrogen.

While a LH-RH agonist or a LH-RH antagonist may be used in one preferred aspect of the present invention, the use of a LH-RH agonist is more preferred.

The components used in the above described aspects of the invention are described in more detail:

By the term "LH-RH agonist" is meant synthetic analogues of the natural luteinizing hormone-releasng hormone (LH-RH), a decapeptide of the structure:
L-pyroglutamyl-L-histidyl-L-tryptophyl-L-seryl-L-tyrosyl-glycyl-L-leucyl-L-arginyl-L-prolylglycyl-NH$_2$ Typical suitable LH-RH agonists include nonapeptides and decapeptides represented by the formula:
L-pyroglutamyl-L-histidyl-L-tryptophyl-L-seryl-L-tyrosyl-X-Y-L-arginyl-L-prolyl-Z
wherein X is D-tryptophyl, D-leucyl, D-alanyl, iminobenzyl-D-histidyl, 3-(2-naphthyl)-D-alanyl, O-tert-butyl-D-seryl, D-tyrosyl, D-lysyl, D-phenylalanyl or N-methyl-D-alanyl and Y is L-leucyl, D-leucyl, N$^α$-methyl D-leucyl, N$^α$-methyl-L-leucyl or D-alanyl and wherein Z is glycyl-NHR$_1$ or NHR$_1$ wherein R$_1$ is H, lower alkyl or lower haloalkyl. Lower alkyl includes straight or branched chain alkyls having 1 to 6 carbon atoms, e.g., methyl, ethyl, propyl, pentyl or hexyls, iso-butyl, neopentyl and the like. Lower haloalkyl includes straight and branched chain alkyls of 1 to 6 carbon atoms having a halogen substituent, e.g., —CF$_3$, —$CH_2CF_3$, —$CF_2CH_3$. Halogen means F, Cl, Br, with F being preferred.

Preferred nonapeptides wherein Y is L-leucyl and X is an optically active D-form of selected amino acids and Z is $NHC_2H_5$ are [D-Trp$^6$, des-gly-$NH_2^{10}$]LH-RH ethylamide (X=D-Trp$^6$); [D-Ser-(t-BuO)$^6$, des-gly-$NH_2^{10}$]—LH-RH ethylamide [X=D-Ser(t-BuO)$^6$]; [D-Leu$^6$, des-gly-$NH_2^{10}$]-LH-RH ethylamide (X=D-Leu6), [D-His(Bzl)$^6$, des-gly $NH_2^{10}$]LH-RH ethylamide (X=iminobenzyl-D-His$^6$) and [D-Ala$^6$, des-gly-$NH_2^{10}$]-LH-RH ethylamide (X=D-Ala$^6$).

Preferred decapeptides include [D-Trp$^6$]-LH-RH wherein X=D-Trp, Y=L-leucyl, Z=glycyl-$NH_2$, [D-Phe$^6$]-LH-RH wherein X=D-phenylalanyl, Y=L-leucyl and Z=glycyl-$HN_2$) or [D-Nal(2)$^6$]LH-RH which is [(3-(2-naphthyl)-D-Ala$^6$]LH-RH wherein X=3-(2-naphthyl)-D-alanyl, Y=L-leucyl and Z=glycyl-$NH_2$.

Other LH-RH agonists useful within the scope of this invention are the α-aza analogues of the natural LH-RH, especially, [D-Phe$^6$, Azgly$^{10}$]-LH-RH, [D-Tyr(-Me)$^6$, Azgly$^{10}$]-LH-RH, and [D-Ser-(t-BuO)$^6$, Azgly$^{10}$]-LH-RH disclosed by A. S. Dutta et al. in J. Med. Chem., 21, 1018 (1978) and U.S. Pat. No. 4,100,274 as well as those disclosed in U.S. Pat. Nos. 4,024,248 and 4,118,483.

Typical suitable LH-RH antagonists include [N-Ac-D-p-Cl-Phe$^{1,2}$, D-Phe$^3$, D-Arg$^6$, D-Ala$^{10}$]-LH-RH disclosed by J. Ercheggi et al., Biochem. Biophys. Res. Common. 100, 915–920, (1981); [N-Ac-D-p-Cl-Phe$^{1,2}$, D-Trp$^3$, D-Arg$^6$, D-Ala$^{10}$]LH-RH disclosed by D. H. Coy et al., Endocrinology, 110: 1445–1447, (1982); [N-Ac-D-(3-(2-naphthyl)-Ala)$^1$, D-p-Cl-Phe$^2$, D-Trp$^3$, D-hArg(Et$_2$)$^6$, D-Ala$^{10}$]-LH-RH and [N-Ac-Pro$^1$, D-p-F-Phe$^2$, (D-(3-(2-naphthyl)Ala$^{3,6}$]-LH-RH disclosed by J. J. Nestor et al. J. Steroid Biochem., 20 (No. 6B), 1366 (1984); the nona - and decapeptides analogs of LH-RH useful as LH-RH antagonists disclosed in U.S. Pat. No. 4,481,190 (J. J. Nestor et al.); analogs of the highly constrained cyclic antagonist, cycle [$\Delta^3$ Pro$^1$, D-p-Cl-Phe$^2$, D-Trp$^{3,6}$, N-Me-Leu$^7$, β-Ala$^{10}$]-LH-RH disclosed by J. Rivier, J. Steroid Biochem., 20, (No. 6B), 1365 (1984), and [N-Ac-D-(3-(2-naphthyl)-Alal$^1$, D-p-F-Phe$^2$, D-Trp$^3$, D-Arg$^6$]-LH-RH disclosed by A. Corbin et al., J. Steroid Biochem. 20 (No. 6B) 1369 (1984).

Other LH-RH agonist and antagonist analogs are disclosed in *LH-RH and Its Analogs*, B. H. Vickery et al. editors at pages 3–10 (J. J. Nestor), 11–22 (J. Rivier et al.) and 23–33 (J. J. Nestor et al.)

The LH-RH agonists and antagonists useful in this invention may conveniently be prepared by the method described by Stewart et al. in "Solid Phase Peptide Synthesis" (published in 1969 by Freeman & Co., San Franciso, page 1) but solution synthesis may also be used.

The nona- and decapeptides used in this invention are conveniently assembled on a solid resin support, such as 1% cross-linked Pro-Merrifield resin by use of an automatic peptide synthesizer. Typically, side-chain protecting groups, well known to those in the peptide arts, are used during the dicyclohexylcarbodiimide-catalyzed coupling of a tert-butyoxycarbonylamino acid to the growing peptide attached to a benzhydrylamine resin. The tert-butyloxycarbonyl protecting groups are removed at each stage with trifluoroacetic acid. The nona- or decapeptide is cleaved from the resin and deprotected by use of HF. The crude peptide is purified by the usual techniques, e.g., gel filtration, HPLC and partition chromatography and optionally lyophilization. See also D. H. et al., J. Med. Chem. 19, pages 423–452, (1976).

Typical suitable antiandrogens include nonsteroidal antiandrogens such as the imidazolidines, especially 1-(3'-trifluoromethyl-4'-nitrophenyl)-4,4-dimethyl-imidazoline-2,5-dione (also called Anandron) described in U.S. Pat. No. 4,097,578, 4'-nitro-3'-trifluoromethylisobutyranilide (also called flutamide) described in U.S. Pat. No. 4,329,364 as well as N-(phenylalkanoyl)aniline derivatives disclosed in U.S. Pat. No. 4,386,080 and the 3,4-disubstituted - branched-chain acylanilides disclosed in U.S. Pat. No. 4,239,776 (A. T. Glen et al). Flutamide is the preferred antiandrogen.

Typical suitable steroidal antiandrogens include 6-chloro-1,2-dihydro-17-(acetyloxy)-3'H-cyclopropa[1,2]pregna-1,4,6-triene-3,20-dione, available under the tradename of Androcur from Schering A.G., W. Berlin and 17α-acetyloxy-6-methylpregna-4,6-diene-3,20-diene, also called megestrol acetate and available from Mead Johnson & Co., Evansille, Ind. under the tradename of Megace.

Typical suitable antiestrogens include those steroidal and non-steroidal antiestrogens such as (1RS,2RS)-4,4'-diacetoxy-5,5'-difluoro-(1-ethyl-2-methylene)di-m-phenylenediacetate, which is available from Biorex under the tradename of Acefluranol, 6α-chloro-16α-methyl-pregn-4-ene-3,20-dione which is available from Eli Lilly & Co., Indianapolis, Ind. under the tradename of Clometherone, 6-chloro-17-hydroxypregna-1,4,6-triene-3,20-dione which is available as the acetate salt from Syntex Labs, Palo Alto, Cal. as Delmadione Acetate, 17-hydroxy-6-methyl-19-norpregna-4,6-diene-3,20-dione which is available from Theramex under the name of Lutenyl, 1-[2-[4-[1-(4-methoxyphenyl)-2-nitro-2-phenylethenyl]phenoxy]ethyl]-pyrrolidine which is available as the citrate salt from Parke-Davis Div. of Warner-Lambert Co., Morris Plains, N.J. under the name of Nitromifene Citrate, substituted aminoalkoxyphenylalkenes such as (Z)-2-[4-(1,2-diphenyl-1-butenyl)phenoxy]-N,N-dimethylethanamine which is available as the citrate salt from Stuart Pharmaceuticals, Wilmington, Del. as Tamoxifen Citrate (see also Belgian patent No. 637,389, Mar. 1964), 3,4-dihydro-2-(p-methoxyphenyl)-1-naphthyl p-[2-(1-pyrrolidinyl)ethoxy]phenyl ketone which is available as the methane sulfonate salt from Eli Lilly & Co. under the tradename of Trioxifene Mesylate, 1-[4'-(2-phenyl)-b 1-(3'-hydroxyphenyl)-2-phenyl-but-1 -ene, which is available from Klinge Pharma, 6-hydroxy-2-(p-hydroxyphenyl)-benzo(b)thien-3-yl[2-(1-pyrrolidinyl)-ethoxyphenyl]ketone which is available from Eli Lilly & Co. (LY-117018), [6-hydroxy-2-(4-hydroxyphenyl)benzo(b)thien-3-yl]-[4-(2-(1-piperdinyl)ethoxy)phenyl]methanone, which is available from Eli Lilly & Co. as the hydrogen chloride salt (LY-156758) and meso-3,4-bis(3'-hydroxyphenyl)-hexane as well as the dimethyl, diprooyl and 3'-acetoxyphenyl analogues which are described in U.S. Pat. No. 4,094,994 and a series of 1-phenyl-alkane and -alkenes, e.g. (E)-3-cyclopentyl-1-(4-hydroxyphenyl)-1-phenyl-1-butene and 2-cyclopentyl-1-[4-hydroxy- or methoxyphenyl]-3-phenyl-2-propen-1-ol and FC-1157 which is available as the citrate salt from Farmos Grouo, Ltd., Turku, Finland (see also Eur. Pat. Appln. EP No. 78,158). It is preferred to use an antiestrogen which shows minimal partial estrogen agonism. FC-1157, LY-117018, LY-156578 and Tamoxifen are the preferred antiestrogens.

The inhibitors of sex steroid biosynthesis found useful in the oresent invention include those compounds which inhibit biosynthesis of sex steroids and precursor sex steroids of adrenal origin, and/or ovarian (or testicular respectively) preferably of ovarian (or testicular respectively) and adrenal origin.

Typical suitable inhibitors of sex steroid biosynthesis include 3-(4-aminophenyl)-3-ethyl-2,6-piperidinedione which is commonly called aminoglutethimide, which is an inhibitor of sex steroid biosynthesis of adrenal but also ovarian and testicular origin and which is available from Ciba Pharmaceutical Co., Summit N.J. under tradename Cytadren, or ketoconazole an effective testicular but also adrenal sex steroid biosynthesis inhibitor which is available from Janssen Pharmaceutica, Piscataway, N.J. under the tradename Nizoral.

When an inhibitor of adrenal sex steroid biosynthesis, e.g., aminoglutethimide is administered, cortisol biosynthesis is blocked. Accordingly; a glucocorticoid, e.g. hydrocortisone is administered in physiological amounts sufficient to maintain normal glucocorticoid levels.

In this invention, the LH-RH agonist or antagonist and antiandrogen and, where applicable, the inhibitor of steroid biosynthesis, hydrocortisone and antiestrogen are administered as pharmaceutical compositions via topical, parenteral or oral means. The LH-RH agonist or antagonist is administered parenterally, i.e., intramuscularly, subcutaneously or intravenously by injection or infusion by nasal drops or by suppository, where applicable intra-vaginally. The LH-RH agonist or antagonist also may be microencapsulated in or attached to a biocompatible, biodegradable polymer, e.g., poly(d,1-lactide-co-clycolide) and subcutaneously or intramuscularly injected by a technicue called subcutaneous or intramuscular depot to provide continuous, slow release of the LH-RH agonist or antagonist over a period of 30 days or longer. The most preferred route of administration of the LH-RH agonist or antagonist is subcutaneous depot injection. Preferably the antiandrogen will be administered orally. Preferably, the inhibitors of sex steroid biosynthesis such as aminoglutethimide and ketoconazole, and antiestrogen when used, are administered orally.

The amount of each component administered is determined by the attending clinicians taking into consideration the etiology and severity of the disease, the patient's condition and age, the potency of each component and other factors. In the combination therapy of selected sex steroid dependent cancers, such as, testicular cancer, ovarian cancer, colon-rectal cancer, renal cancer, pancreatic cancer, liver cancer, stomach cancer, skin cancer, uterine cancer, brain cancer and larynx cancer, according to this invention, the following dosage ranges are suitable.

The LH-RH agonist or antagonist is generally administered at from about 10 to 5000 $\mu$g per day with contemplated dosage ranges of about 10 to 1500 $\mu$g per day and about 250 (preferably 200 $\mu$g in the therapy of uterine cancer using the combination with sex hormone biosynthesis inhibitor) to 500 $\mu$g per day for the LH-RH agonist and to about 50 to 5000 $\mu$g per day for the LH-RH antagonist being preferred.

In the most preferred embodiment of this invention, the LH-RH agonist or antagonist is administered subcutaneously in a daily dose of 500 $\mu$g for the first 30 days and thereafter subcutaneously in a daily dose of 250 $\mu$g regardless of the patients' body weight. When the LH-RH agonist or antagonist is administered, once every 30-day period or even longer, by intramuscular or subcutaneous depot injection, a dose from about 300 to 150,000 $\mu$g per 30-day period is used, with a dose of 750 to 15,000 $\mu$g per 30-day period being preferred.

The antiandrogen compositions are generally administered in a dosage range of about 0.20 to 40 mg/kg (body weight) per day with 750 mg per day in three equally divided doses being preferred.

The aminoglutethimide compositions (when used) are administered initially in a dosage of 250 mg given at 8-hour intervals and the dosage may be increased in increments of 250 mg daily up to a total daily dose of 2 grams.

The ketoconazole compositions (when used) are administered orally in a dose of 250 mg given at 8-hour intervals and may be increased to a daily dose of 2 grams.

Other inhibitors of sex steroid biosynthesis are preferably administered in dosages being equivalent to the dosages given for aminoglutethimide and ketoconazole.

The antiestrogen compositions (when used) are administered in a dosage range of about 0.1 to 10 mg/kg body weight per day, with 10 mg, especially 20 mg, in two equally divided doses being preferred.

The glucocorticoide, especially hydrocortisone compositions (when used) are administered orally in a dosage range of about 0.1 to 20 mg/kg body weight per day. Preferably, the hydrocortisone is administered orally at the dose of about 10 mg in the morning and about 5 mg doses in the afternoon and in the evening.

The LH-RH agonist or antagonist and antiandrogen and inhibitor of sex steroid bisoynthesis and antiestrogen (when used) each may be administered separately or when the modes of administration are the same, all or at least two of them may be administered in the same composition, but in any case the preferred ratio of LH-RH agonist to antiandrogen to antiestrogen (when used) to inhibitor of sex steroid biosynthesis (when used) administered daily will be about 250 $\mu$g of LH-RH aqonist to about 750 mg of antiandrogen to about 15 mg, especially 20 mg, of anti-estrogen to about 750 mg of inhibitor of sex steroid biosynthesis.

In the therapy of selected sex steroid dependent cancers such as, for example, uterine cancer combining the administration of an LH-RH agonist or antagonist, an antiandrogen and an antiestrogen the dosages preferable are as follows: The LH-RH agonist or antagonist is generally administered at from about 10 to 2000 $\mu$g per day, with contemplated dosage ranges of 10 to 500 $\mu$g per day, 50–250 $\mu$g per day and 250 to 500 $\mu$g per day being preferred. In the most preferred embodiment of this aspect of the invention, the LH-RH agonist or antagonist is administered subcutaneously in a daily dose of 500 $\mu$g for the first 30 days and thereafter subcutaneously in a daily dose of 250 $\mu$g regardless of the patients' body weight. When the LH-RH agonist or antagonist is administered, once every 30-day period, by intramuscular or subcutaneous depot injection, a dose from about 300 to 60000 (occasionally 15000) $\mu$g per 30-day period is used, with a dose of 750 to 6000 $\mu$g per 30-day period being preferred. The antiandrogen compositions are generally administered in a dosage range of about 0.20 to 20 preferably 40 mg/kg (body weight) per day with 375 especially 750 mg per day in three equally divided doses being preferred. The antiestrogen compositions are administered in a dosage range of about 0.1 to 10 mg/kg body weight per day, with 15 mg in three, preferably with 20 mg in two, equally divided doses being preferred. The aminoglutethimide compositions when used are administered initially in a dosage of 250 mg given at 6-hour, preferably 8-hour, intervals and the dosage may be increased in increments of 250 mg daily up to a total daily dose of 2 grams. The ketoconazole compositions when used are administered orally in a dose of 200 mg once per day and may be increased to 800 mg once per day.

The LH-RH agonist or antagonist and antiandrogen and antiestrogen each may be administered separately or when the modes of administration are the same, all or two of them may be administered in the same composition, but in any case the preferred ratio of LH-RH agonist to antiandrogen to antiestrogen administered daily will be about 250 μg of LH-RH agonist to about 375 especially 750 mg of antiandrogen to about 15, preferably 20, mg of antiestrogen.

In the therapy of the selected sex steroid dependent cancers, according to this invention, it is preferred that the LH-RH agonist is [D-Trp$^6$,des-Gly NH$_2$$^{10}$]LH-RH ethylamide which is administered subcutaneously in single daily dose of 500 μg for the first thirty (30) days of treatment and thereafter in a single daily dose of 250 μg; the antiandrogen is 4'-nitro-3'-trifluoromethyl-isobutyranilide, i.e. flutamide, which is administered orally in three equally divided daily doses of 250 mg each; and the inhibitor of sex steroid biosynthesis is ketoconazole and/or aminoglutethimide, each of which is administered orally in three equally divided doses of 250 mg every 8 hours; and the hydrocortisone (if used) is administered orally at a dose of about 10 mg in the morning and two equally divided doses of about 5 mg, 8 and 16 hours thereafter; and the antiestrogen, when used, is (Z)-2-[p-(1,2-diphenyl-1-butenyl)phenoxy]-N,N-dimethyl ethylamine (Tamoxifen) which is administered orally in two equally divided oses of about 10 mg every 12 hours. In the therapy of, for example, uterine cancer using the combination of the LH-RH agonist, the antiandrogen and antiestrogen discussed here, it is also useful to administer the antiandrogen (flutamide) orally in three equally divided doses of 125, preferably 250 mg.

In the combination therapy of the selected sex steroid dependent cancers according to this invention the administration of the antiandrogen, antiestrogen, inhibitor(s) of steroid biosynthesis, glucocorticoid and LH-RH agonist or LH-RH antagonist can be started in any order of sequence. Preferably the administration of the antiandrogen and/or the antiestrogen is started before (preferably one day before) the administration of the LH-RH agonist or LH-RH antagonist is started. Preferably the administration of the inhibitor(s) of sex steroid biosynthesis is started on the same day as the administration of the LH-RH agonist or LH-RH antagonist. However, the attending clinician may elect to start administration of the LH-RH agonist or antagonist on the first day of treatment.

When patients whose testes or ovaries respectively have already been surgically removed are treated according to this invention, the administration and dosage of the antiandrogen and the other components of the therapy (exceot the LH-RH agonist or antagonist) are the same as indicated for the therapy in which the LH-RH agonist or antagonist is used.

Normally, an inhibitor of testicular sex steroid biosynthesis such as ketoconazole may be administered to chemically but not surgically castrated patients.

Generally, the inhibitor of testicular sex steroid biosynthesis (when used), e.g., ketoconazole will be administered until the serum levels of T and DHT stimulated by the administration of the LH-RH agonist are effectively suppressed, normally for one to three weeks. The inhibitor of adrenal sex steroid biosynthesis, e.g., aminoglutethimide may be administered at the start of treatment in the presence or absence of the inhibitor of testicular sex steroid biosynthesis and thereafter continued throughout the period of treatment.

The LH-RH agonists or antagonists useful in the present invention are typically amorphous solids which are freely soluble in water or dilute acids, e.g., HCl, H$_2$SO$_4$, citric, acetic, mandelic or fumaric. The LH-RH agonist or antagonist for subcutaneous injection is supplied in vials containing 5 mL of sterile solution with the LH-RH agonist or antagonist at a concentration of about 1.0 mg/mL.

A typical pharmaceutical composition of the LH-RH agonist or antagonist include the LH-RH agonist or antagonist or a pharmaceutically acceptable acid salt thereof, benzyl alcohol, a phosphate buffer (pH=6.9–7.2) and sterile water.

The LH-RH agonist or antagonist for intramuscular or subcutaneous depot injection may be microencapsulated in a biocompatible, biodegradable polymer, e.g., poly (d,l-lactide-co-glycolide) by a phase separation process or formed into a pellet. The microspheres may then be suspended in a carrier to provide an injectable preparation or the depot may be injected in the form of a pellet. See also European patent application EPA No. 58,481 published Aug. 25, 1982 for solid compositions for subdermal injection or implantation or liguid formulations for intramuscular or subcutaneous injections; containing biocompatible, biodegradeable polymers such as lactide-glycolide copolymer and an LH-RH agonist, e.g., D-Ser-t-BuO$^6$, Azgly$^{10}$-LH-RH.

The inhibitors of sex steroid biosynthesis, e.g., aminoglutethimide and ketoconazole and the glucocorticoid, e.g., hydrocortisone (when used) are typically compounded in customary ways for oral administration, e.g., in tablets, capsules and the like.

The antiandrogens useful in the present invention are typically formulated with conventional pharmaceutical excipients, e.g., spray dried lactose and magnesium stearate into tablets or capsules for oral administration. The antiestrogens, when used with the invention, are typically compounded in customary ways for oral administration, e.g., in capsules, tablets, as dragees or even in liquid form, e.g., suspensions or syrups. One or more of the active substances, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycols. Of course, taste-improving substances can be added in the case of oral-administration forms.

The therapeutically active antiestrogen compound should be present in a concentration of about 0.5–90% by weight of the total mixture, i.e., in amounts that are sufficient for maintaining the above-mentioned dosage range.

As further forms of administration, one can use plug capsules, e.g., of hard gelatin, as well as closed soft-gelatin capsules comprising a softener or plasticizer, e.g., glycerine. The plug capsules contain the active substance preferably in the form of granulate, e.g., in mixture with fillers, such as lactose, saccharose, mannitol, starches, such as potato starch or amylopectin, cellulose derivatives or highly-dispersed silicic acids. In soft-gelatin capsules, the active substance is preferably dissolved or suspended in suitable liquids, such as vegetable oils or liquid polyethylene glycols.

In place of oral administration, the active compounds may be administered parenterally. In such case, one can use a solution of the active substance, e.g., in sesame oil or olive oil.

Following the above treatment using the described regimen, tumor growth and bone metastases of sex steroid dependent cancers is inhibited and in some instances complete remission occurs.

The invention also provides kits or single packages combining the pharmaceutical compositions useful for the combination treatment of the selected sex-steroid dependent cancers discussed above. The kits or packages may also contain instructions to use the pharmaceutical compositions in accordance with the present invention. This aspect of the invention is exemplified by the following discussions: For the treatment of uterine or renal cancer a two component kit provides the antiandrogen oral pharmaceutical composition and the LH-RH agonist or LH-RH antagonist parenteral composition or the antiandrogen oral pharmaceutical composition and the antiestrogen oral composition or the oral compositions of the antiandrogen or antiestrogen and the inhibitor of sex steroid biosynthesis; a three component kit provides the LH-RH agonist or antagonist parenteral pharmaceutical composition, the antiandrogen and the antiestrogen oral pharmaceutical composition, or the oral compositions of the antiandrogen, the antiestrogen and the inhibitor of sex steroid biosynthesis; a four component kit provides the LH-RH agonist or LH-RH antagonist parenteral pharmaceutical composition, the antiandrogen oral pharmaceutical composition, the sex steroid biosynthesis inhibitor oral pharmaceutical composition and the hydrocortisone oral pharmaceutical composition; and a five component kit provides the LH-RH agonist or LH-RH antagonist parenteral pharmaceutical composition, the antiandrogen oral pharmaceutical composition, the antiestrogen oral pharmaceutical composition, the sex steroid biosynthesis inhibitor oral composition and the hydrocortisone oral pharmaceutical composition. Further kits are provided in accordance with the combination therapy of this invention.

For the treatment of renal or uterine cancer, a three component kit provides the antiandrogen oral pharmaceutical composition, the LH-RH agonist or LH-RH antagonist parenteral composition and the sex steroid biosynthesis inhibitor oral pharmaceutical composition; a four component kit provides the LH-RH agonist or LH-RH antagonist parenteral pharmaceutical composition, the antiandrogen oral pharmaceutical composition, the adrenal sex steroid biosynthesis inhibitor oral pharmaceutical composition and the hydrocortisone oral pharmaceutical composition; and a five component kit provides the LH-RH agonist or LH-RH antagonist parenteral pharmaceutical composition, the antiandrogen oral pharmaceutical composition and the testicular sex steroid biosynthesis inhibitor oral pharmaceutical composition, the adrenal sex steroid biosynthesis inhibitor oral pharmaceutical composition and the hydrocortisone oral pharmaceutical composition. Further kits are provided in accordance with the combination therapy of this invention.

For the treatment of other sex steroid dependent cancers analogous kits are provided according to this invention. The kits may also contain pharmaceutical compositions which contain more than one component of the combination treatment.

The following example illustrates the invention.

EXAMPLE 1

Figure 1:
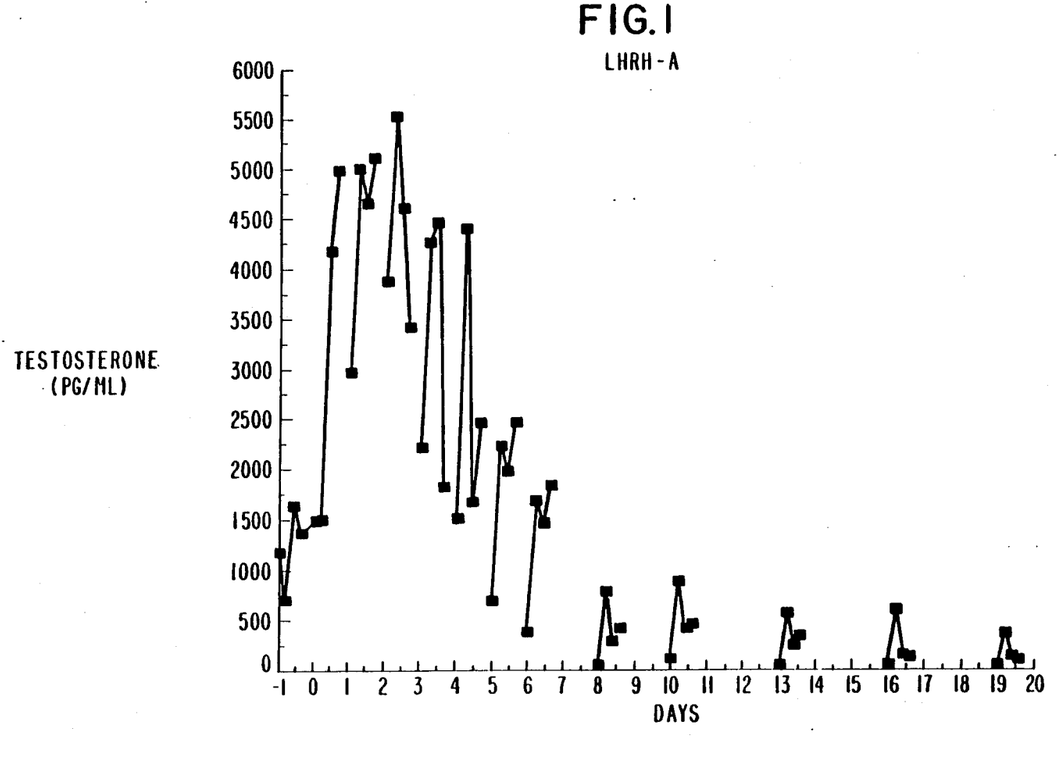
FIG. 1 shows testosterone serum levels in dogs during daily treatment with [D-Trp$^6$, des-Gly-NH$_2^{10}$]LH-RH ethylamide (LHRH-A).
Figure 2:
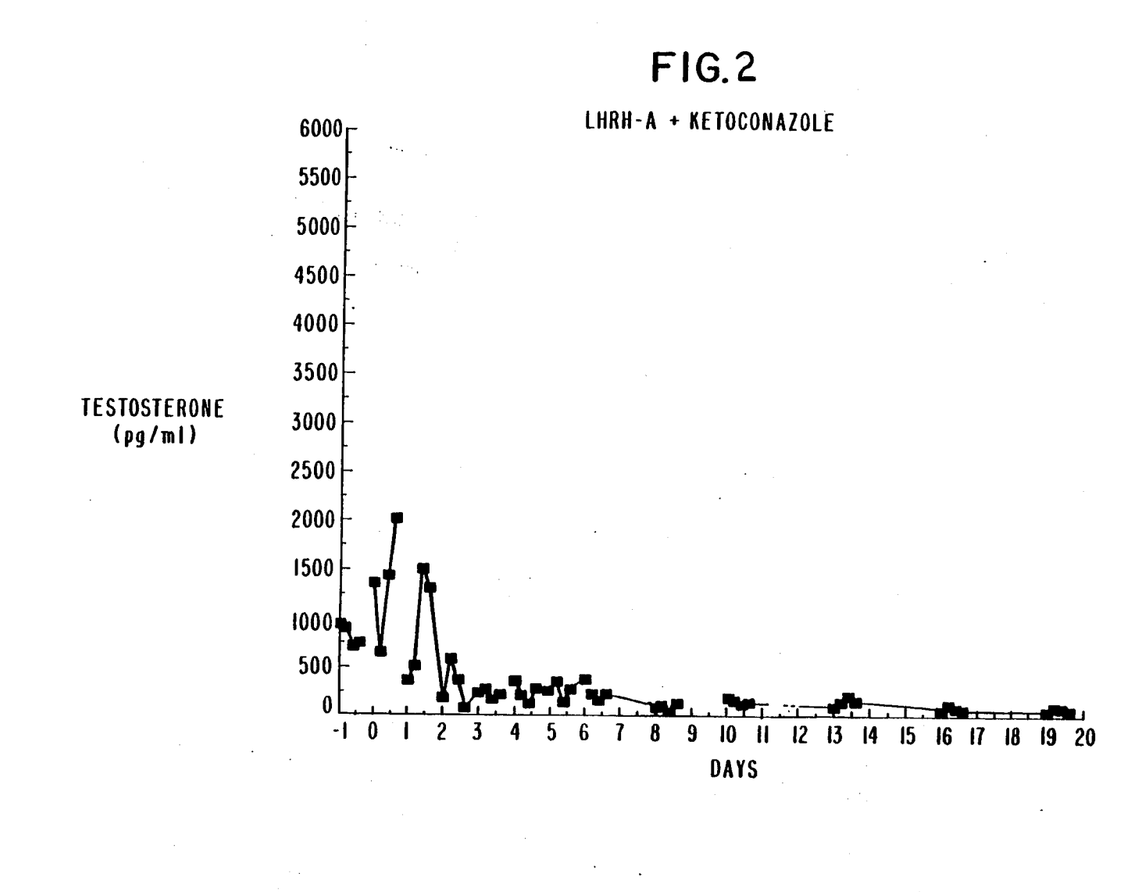
FIG. 2 shows testosterone serum levels in dogs during daily treatment with LHRH-A in association with ketoconazole.
Figure 3:
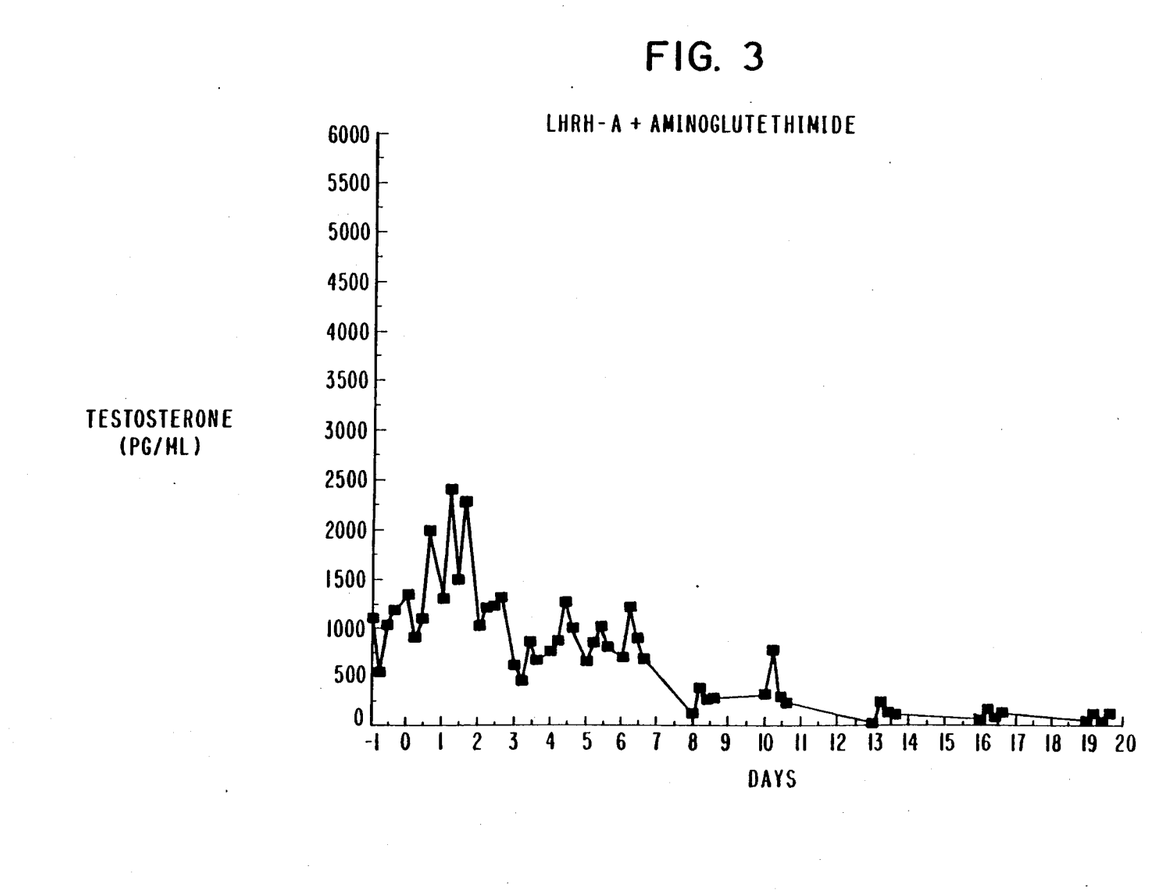
FIG. 3 shows testosterone serum levels in dogs during daily treatment with LHRH-A in association with aminoglutethimide.

Inhibitory Effect of Aminoglutethimide or Ketoconazole on LHRH Agonist-Induced Serum Testosterone in the Dog FIGS. 1 to 3 show the result of the test.

FIG. 1. Serum levels of testosterone during the first 19 days of treatment of dogs with daily administration of 50 $\mu$g of [D-Trp$^6$, des-Gly-NH$_2$$^{10}$]LHRH ethylamide.

FIG. 2. Serum levels of testosterone during the first 19 days of treatment of dogs with daily administration to 50 $\mu$g of [D-Trp$^6$, des-Gly-NH$_2$$^{10}$]LHRH ethylamide in association with ketoconazole.

FIG. 3. Serum levels of testosterone during the first 19 days of treatment of dogs with daily administration of 50 $\mu$g of [D-Trp$^6$, des-Gly-NH$_2$$^{10}$]LHRH ethylamide in association with aminoglutethimide.

While LHRH agonists achieve castration levels of androgens during chronic treatment in men, the first 5 to 10 days of administration of the peptide are associated with increased serum levels of testosterone and dihydrotestosterone (Labrie et al., J. Androl. 1: 209-228, 1980). These increased levels of testicular androgens are accompanied by an exacerbation of the symptoms and signs of prostate cancer in significant proportion of cases (Kahan et al., The Lancet, I, 971-972, 1984).

The following experiment shows that the LHRH agonist-induced rise in serum testosterone can be prevented by simultaneous administration of the steroid biosynthesis inhibitors aminoglutethimide or ketoconazole.

Eighteen mongrel dogs weighing between 20–30 kg were randomly divided into three groups. The animals were housed one per cage and fed Purina Dog Chow and tap water ad libitum.

The animals of group 1 were injected daily (at 0700 h) with 50 $\mu$g of the LHRH agonist [D-Trp$^6$, des-Gly-NH$_2$$^{10}$]LHRH ethylamide (LHRH-A). In group 2, the animals were also injected daily with 50 $\mu$g of LHRH-A and took in addition 200 mg of ketoconazole per os at 0700 h, 1500 h and 2300 h. The animals of group 3 received daily 50 $\mu$g of LHRH-A and 125 mg of aminoglutethimide per os at 0700 h, 1500 h, 2300 h plus 10 mg of hydrocortisone twice daily.

Blood samples were collected at 0700 h, 0900 h, 1100 h and 1500 h one day before treatment and every day during the treatment. Plasma was extracted with diethyl ether and testosterone was separated on LH-20 columns before RIA measurements.

FIG. 1 shows that on one to six days following the start of treatment with the daily injection of 50 $\mu$g of the LHRH agonist [D-Trp$^6$des-Gly-NH$_2$$^{10}$]LHRH ethylamide, there is an increase in serum testosterone up to approximately 500% above control. Thereafter, there is a decrease of the level of this androgen which reaches near-castration levels on day 19. It can be seen in FIGS. 2 and 3 that the simultaneous administration of the steroid inhibitors ketoconazole or aminoglutethimide almost completely prevented this rise in serum testosterone which occur during the first days of treatment with the peptide.

These data clearly indicate the usefulness of the combined administration of inhibitors of steroid biosynthesis in order to prevent the rise of testicular serum androgens during the first days of treatment with LHRH agonists.

Since dogs do not have adrenal production of androgens the influence of the administration of an antiandrogen in combination with the administration of the LH-RH agonist and the inhibitors of sex steroid biosynthesis cannot be demonstrated in this species. However, it can be concluded from the test results that in men the administration of an antiandrogen (especially flutamide) in combination with the LH-RH agonist or antagonist and the inhibitors of sex steroid biosynthesis which inhibit the secretion of precursor adrenal androgens substantially or completely decreases the content of androgens in the system and thus contributes to the inhibition of androgen sensitive cancer growth.

What is claimed is:

1. A method of treating selected sex steroid dependent cancers in a warm-blooded animal which comprises administering a therapeutically effective amount of an antiandrogen and/or an antiestrogen and/or at least one inhibitor of sex steroid biosynthesis or pharmaceutical compositions thereof to the animal whose hormone output of the testes or ovaries is blocked; wherein the selected sex steroid dependent cancers are testicular cancer, ovarian cancer, colon-rectal cancer, renal cancer, pancreatic cancer, liver cancer, stomach cancer, skin cancer, uterine cancer, brain cancer or larynx cancer.

2. A method according to claim 1 which for treating testicular cancer, ovarian cancer, colon-rectal cancer, renal cancer, pancreatic cancer, liver cancer, stomach cancer, skin cancer, uterine cancer, brain cancer and larynx cancer comprises administrating a therapeutically effective amount (1) of an antiandrogen or (2) of at least one inhibitor of sex steroid biosynthesis or (3) of an antiandrogen and an antiestrogen or (4) of an antiandrogen and at least one inhibitor of sex steroid biosynthesis or (5) of an antiestrogen and at least one inhibitor of sex steroid biosynthesis or (6) of an antiandroqen and an antiestrogen and at least one inhibitor of sex steroid biosynthesis or pharmaceutical compositions thereof.

3. A method according to any one of claims 1 which further comprises administration of a glucocorticoi<.

4. A method according to claim 1 wherein the antiandrogen and/or the antiestrogen and/or at least one inhibitor of sex steroid biosynthesis and, if used, the glucocorticoid is/are administered to an animal whose hormone output of the testes or ovaries, has been blocked by surgical removal thereof.

5. A method according to claim 1 wherein the antiandrogen and/or the antiestrogen and/ or at least one inhibitor of sex steroid biosynthesis and, if used, the glucocorticoid is/are administered to an animal whose hormone output of the testes or ovaries is blocked by chemical means such as by an LH-RH agonist or LH-RH antagonist of which a pharmaceutically effective amount is administered to the animal in association with the antiandrogen and/or the antiestrogen and/or the inhibitor(s) of steroid biosynthesis and/or the glucocorticoid.

6. A method according to claim 1 which comprises administering the antiandrgoen, the antiestrogen, the inhibitor(s) of sex steroid biosynthesis, the LH-RH agonist or LH-RH antagonist and the glucocorticoid (if applicable) in the form of individual compositions.

7. A method according to claim 6 wherein the administration of the antiandrogen and/or the antiestrogen is started one day before the administration of the LH-RH agonist or LH-RH antagonist and of the inhibitor(s) of sex steroid biosvnthesis (if used) and the glucocorticoid (if used).

8. A method according to claim 7 which comprises administering the LH-RH agonist or LH-RH antagonist in the form of parenteral composition.

9. A method according to claim 1 which comprises administering the antiandrogen, antiestrogen, the inhibitor(s) of sex steroid biosynthesis and the glucocorticoid in the form of oral compositions.

10. A method according to claim 1 wherein the antiandrogen is 4'-nitro-3'-trifluoromethylisobutyranilide or 1-(3'-trifluoromethyl-4'-nitrophenyl)-4,4-dimethylimidazoline-2,5-dione.

11. A method according to claim 5 wherein the LH-RH agonist is a nonapeptide or a decapeptide represented by the formula: L-pyroglutamyl-L-histidyl-L-tryptophyl-L-seryl-L-tyrosyl-X-Y-L-arginyl-L-prolyl-Z, wherein X is D-tryptophyl, D-leucyl, D-alanyl, iminobenzyl-D-histidyl, 3-(2-naphthyl)-D-alanyl, O-tert-butyl-D-seryl, D-tyrosyl, D-lysyl, D-phenylalanyl or N-methyl-D-alanyl and wherein Y is L-leucyl, $N^{\alpha}$-methyl-L-leucyl, D-leucyl, $N^{\alpha}$-methyl-D-leucyl, or D-alanyl and wherein Z is glycyl-$NHR_1$ or $NHR_1$ wherein $R_1$ is H, lower alkyl or haloloweralkyl.

12. A method according to claim 1 wherein aminoglutethimide and/or ketokonazole are used as inhibitors of sex steroid biosynthesis.

13. A method according to claim 1 wherein the antiestrogen is (Z)-2-[4-(1,2-diphenyl-1-butenyl)phenoxy]-N,N-dimethylethanamine or LY-117018.

* * * * *